United States Patent
Gupta et al.

(10) Patent No.: US 10,318,839 B2
(45) Date of Patent: Jun. 11, 2019

(54) METHOD FOR AUTOMATIC DETECTION OF ANATOMICAL LANDMARKS IN VOLUMETRIC DATA

(71) Applicants: Council of Scientific and Industrial Research, New Delhi (IN); National Informatics Centre—Department of Electronics and Information Technology, New Delhi (IN)

(72) Inventors: Abhishek Gupta, Chandigarh (IN); Harish Kumar Sardana, Chandigarh (IN); Om Prakash Kharbanda, New Delhi (IN); Viren Sardana, Chandigarh (IN)

(73) Assignees: Council of Scientific and Industrial Research, New Delhi (IN); National Informatics Centre Department of Electronics and Information Technology, New Delhi (IN)

( * ) Notice: Subject to any disclaimer, the term of this patent is extended or adjusted under 35 U.S.C. 154(b) by 115 days.

(21) Appl. No.: 14/994,044

(22) Filed: Jan. 12, 2016

(65) Prior Publication Data
US 2016/0203604 A1 Jul. 14, 2016

(30) Foreign Application Priority Data
Jan. 13, 2015 (IN) .............................. 94/DEL/2015

(51) Int. Cl.
*A61C 7/00* (2006.01)
*G06K 9/46* (2006.01)
(Continued)

(52) U.S. Cl.
CPC ............ *G06K 9/4604* (2013.01); *A61C 7/002* (2013.01); *G06K 9/3233* (2013.01); *G06K 9/52* (2013.01);
(Continued)

(58) Field of Classification Search
CPC ....... A61C 7/002; A61C 7/00; A61C 13/0004; A61B 6/14; A61B 6/469; A61B 6/032;
(Continued)

(56) References Cited

U.S. PATENT DOCUMENTS

| | | | | | |
|---|---|---|---|---|---|
| 5,760,778 | A | * | 6/1998 | Friedman | G06K 9/468 345/420 |
| 6,078,688 | A | * | 6/2000 | Cox | G06T 7/162 382/173 |

(Continued)

OTHER PUBLICATIONS

Chen et al., Automatic X-ray landmark detection and shape segmentation via data-driven joint estimation of image displacements, Apr. 2014 [retrieved Jun. 23, 2017], Medical Image Analysis, vol. 18, Issue 3,pp. 487-499. Retrieved from the Internet: http://www.sciencedirect.com/science/article/pii/S1361841514000048.*

(Continued)

*Primary Examiner* — Andrew M Moyer
*Assistant Examiner* — Dennis Rosario
(74) *Attorney, Agent, or Firm* — Knobbe, Martens, Olson & Bear, LLP (57) ABSTRACT

Embodiments of a method for detection of plurality of three-dimensional cephalometric landmarks in volumetric data are disclosed. In some embodiments, a three-dimensional matrix is developed by stacking of volumetric data and the bony structure is segmented through thresholding. Initially a seed point is searched for initializing the process of landmark detection. Two three-dimensional distance vectors are used to define and obtain the Volume of Interest (VOI). First 3-D distance vector helps to identify Empirical Point and consecutively second gives dimensions of the VOI. Three-dimensional contours of anatomical structure are traced in the estimated VOI. Cephalometric landmarks are identified on the boundaries of traced anatomical geometry, based on corresponding Mathematical Entities.

(Continued)

Detected landmark can be used as a Reference Point for further detection of landmarks. Estimating the VOI and detection of points continues till all desired landmarks are detected. The detection procedure gives three-dimensional coordinate locations of the landmarks.

19 Claims, 4 Drawing Sheets (51) Int. Cl.
  *G06K 9/52* (2006.01)
  *G06T 7/00* (2017.01)
  *G06K 9/32* (2006.01)
(52) U.S. Cl.
  CPC ...... *G06T 7/0012* (2013.01); *G06K 2209/055* (2013.01); *G06T 2200/04* (2013.01); *G06T 2207/10081* (2013.01); *G06T 2207/10088* (2013.01); *G06T 2207/30036* (2013.01)
(58) Field of Classification Search
  CPC ......... A61B 8/483; A61B 5/055; A61B 34/20; A61B 34/10; A61B 2034/105; A61B 5/1075; A61B 6/501; G06T 7/0012; G06T 15/08; G06T 2207/10081; G06T 7/11; G06T 2210/41; G06T 2207/10088; G06T 2207/10072; G06T 2207/30004; G06T 2207/30036; G06T 2207/30008; G06T 17/00
  See application file for complete search history.

(56) References Cited

U.S. PATENT DOCUMENTS

| | | | |
|---|---|---|---|
| 6,674,883 B1* | 1/2004 | Wei | A61F 2/4657 382/132 |
| 7,783,090 B2 | 8/2010 | Nagaraja Rao et al. | |
| 8,023,706 B2 | 9/2011 | Witte | |
| 8,116,544 B2* | 2/2012 | Masumoto | A61B 5/1075 378/1 |
| 8,126,240 B2* | 2/2012 | De Bruijne | A61B 6/505 382/128 |
| 8,150,498 B2 | 4/2012 | Gielen et al. | |
| 8,160,322 B2 | 4/2012 | Dikmen et al. | |
| 8,160,323 B2* | 4/2012 | Zhou | G06K 9/6857 382/128 |
| 8,160,677 B2 | 4/2012 | Gielen et al. | |
| 8,218,849 B2 | 7/2012 | Lu et al. | |
| 8,363,918 B2 | 1/2013 | Schwing et al. | |
| 9,078,621 B2* | 7/2015 | Garner | A61B 5/4504 |
| 9,084,629 B1* | 7/2015 | Rosa | A61B 5/032 |
| 9,153,022 B2* | 10/2015 | Finkelstein | A61B 5/1075 |
| 9,218,542 B2* | 12/2015 | Zhan | G06K 9/6217 |
| 9,480,439 B2* | 11/2016 | Wu | A61B 6/505 |
| 9,554,868 B2* | 1/2017 | Regazzoni | A61B 90/36 |
| 2016/0063720 A1* | 3/2016 | Han | G06T 7/10 382/131 |

OTHER PUBLICATIONS

Gribel et al., Accuracy and reliability of craniometric measurements on lateral cephalometry and 3D measurements on CBCT scans, Jan. 2011 [retrieved Jan. 11, 2019], The Angle Orthodontist, vol. 81, No. 1,pp. 26-35. Retrieved from the Internet: http://www.angle.org/doi/abs/10.2319/032210-166.1 (Year: 2011).*

Grau et al., Automatic Localization of Cephalometric Landmarks, Jun. 2001 [retrieved Jan. 11, 2019], Journal of Biomedical Informatics, vol. 34, Issue 3, pp. 146-156. Retrieved from the Internet: https://www.sciencedirect.com/science/article/pii/S1532046401910147?via%3Dihub (Year: 2001).*

S. Shahidi, E. Bahrampour, E. Soltanimehr, A. Zamani, M. Oshagh, M. Moattari, et al., "The accuracy of a designed software for automated localization of craniofacial landmarks on CBCT images," BMC Med Imaging, vol. 14, pp. 1471-2342, 2014.

S. Cauter et al. "3D cephalometry: a new approach for landmark identification and image orientation" IFMBE Proceedings 2008.

* cited by examiner

METHOD FOR AUTOMATIC DETECTION OF ANATOMICAL LANDMARKS IN VOLUMETRIC DATA

CROSS-REFERENCE TO RELATED APPLICATIONS

This application claims the benefit of the Indian Application No. 94/DEL/2015, which was filed on Jan. 13, 2015, and which is hereby incorporated by reference in its entirety.

BACKGROUND

Technical Field

The present disclosure relates to the field of cephalometric analysis in orthodontics. More particularly, the disclosure relates to the method of automated cephalometric landmark detection on volumetric data, used by orthodontic specialists in cephalometric analysis for diagnosis and treatment planning of their patients.

Description of the Related Art

In dentistry, Orthodontic specialists use cephalometric analysis for diagnosis and treatment planning of patient's dento-maxillofacial and craniofacial deformity. In case of surgery, growth prediction or evaluation, monitoring treatment outcome cephalometric analysis is needed. It is based on geometrical measurements such as distances and angle. These measurements are recorded among standardly defined anatomical points called as landmarks. Calculated measurements of a patient are compared with standardly existing normal values according to the patient's race and ethnicity.

In the past, measurements, calculation and analysis were conducted manually by placing tracing sheets on the X-Ray film, which was error prone. Currently, computerized analysis is in clinical practice. Analysis is performed using plotted cephalometric landmarks on scanned/digital 2-D X-Ray films or 3-D CT/CBCT scan volumetric data of the skull. Plotting of landmarks takes time and efforts of an orthodontic specialist thus being tedious and time consuming. Also repeatability and reproducibility may be affected. Hence, computerized 2-D cephalometric analysis software is available for helping orthodontist. Analysis on three-dimensional frame is used to avoid the problems in two-dimensional radiographs. But, manual marking and plotting of landmarks on 3-D data is more difficult and exhausting with the appearance of third dimension. Thus, a method is proposed for searching landmarks automatically on 3-D volumetric data for assisting orthodontic surgeons.

The prior art uses marginal space learning geometrical model for localization of 3-D landmarks. It requires a training set for correct position and orientation. Hence, accuracy is not promising due to localization of points on the basis of distance learning based training. Another approach aligns patient image and training image of already localized points, using positional scaling and rotation. Then, correct position of a point is searched using similarity search for a feature. As the patient geometry is variable, results from similarity search are not promising. Another approach uses image adaptive transformation with already traced cephalometric image for anatomical landmark detection. This approach is similar as registration of two images.

At least some of the disclosed embodiments do not use any training set or registration procedure. In some embodiments, clustering of certain landmarks in a group and corresponding region is identified using Empirical Point calculated from a reference point. Corresponding Mathematical. Entity on detected contour gives the location of cephalometric landmark.

In contrast, prior art suffers from at least the following drawbacks.

U.S. Pat. No. 8,023,706 B2 Sep. 20, 2011 Automatically Determining Landmarks On Anatomical Structure This patent discloses converting sample image into patient image, by transforming anatomical structure of sample data into anatomical structure of patient data using morphing and image fusion algorithms. Similarly, cephalometric landmarks are identified on patient image by transformation of a sample image.

The transformation of sample image to a patient image is the drawback of this patent. By transformation of a standard image cannot promise for accurate results on the patient image.

U.S. Pat. No. 8,363,918 B2 Jan. 29, 2013 Method and System For Anatomic Landmark Detection Using Constrained Marginal Space Learning And Geometric Interface This patent discloses detecting first landmark using Marginal Space Learning (MSL) and remaining landmarks based on geometrical model. Geometrical model is trained with manual cephalometric landmarks on various datasets.

The drawback of this system is that it has to calculate object position, position orientation and similarity transformation factors for transforming learned geometrical model to patient three-dimensional model. The estimation of these factors from trained model does not promise for accurate measure of cephalometric landmark position, U.S. Pat. No. 8,160,322 B2 Apr. 17, 2012 Joint Detection And Localization Of Multiple Anatomical Landmarks Through Learning This patent discloses detecting anatomical landmarks in medical images and verifies its locations through spatial statistics.

The system is made for detecting anatomical landmarks using training database classifiers. The approach of the patent is generic for whole body anatomical landmarks. It comments neither for 2D or 3D landmarks nor for cephalometric landmarks in specific.

U.S. Pat. No. 8,218,849 B2 Jul. 10, 2012, Method And System For Automatic Landmark Detection Using Discriminative Joint Context This patent discloses detecting anatomical landmarks in heart Magnetic Resonance Imaging (MRI) using joint context. This method cannot be applied for cephalometric landmark detection.

U.S. Pat. No. 8,160,677 B2 Apr. 17, 2012 Method For Identification of Anatomical Landmarks This patent discloses detecting anatomical landmarks in brain Magnetic Resonance Imaging (MRI) and a combination of steps cannot be applied for cephalometric landmark detection.

U.S. Pat. No. 8,150,498 B2 Apr. 3, 2012 System For Identification Of Anatomical Landmarks This patent discloses detecting anatomical landmarks in brain Magnetic Resonance Imaging (MRI) and a combination of steps cannot be applied for cephalometric landmark detection.

U.S. Pat. No. 7,783,090 B2 Aug. 24, 2010 Automatic Identification Of The Anterior And Posterior Commissure Landmarks This patent discloses detecting anterior and posterior commissure landmarks in brain Magnetic Resonance Imaging (MRI) and a combination of steps cannot be applied for cephalometric landmark detection.

S. Shahidi, E. Bahrampour, E. Soltanimehr, A. Zamani, M. Oshagh, M. Moattari, et al., "The accuracy of a designed software for automated localization of craniofacial landmarks on CBCT images," BMC Med Imaging, vol. 14, pp. 1471-2342, 2014

This work proposed a method of automatic landmark detection based on the registration of test image over training image dataset. Registration is based on translation, rotation and scaling of training image and test image in all three axes. Translation is based on the center of gravity and principal axes of the 3D image, The anatomy of each patient has a unique geometrical structure; therefore it cannot be overlapped properly over the anatomy of training data. Hence, the translation of landmarks from training to test image is error prone and promising results cannot be obtained.

S. Canter et al. "3D cephalometry: a new approach for landmark identification and image orientation" IFMBE Proceedings 2008

This work explained a method of 3-D semi-automatic cephalometric landmark detection. A small region of points is detected manually which is a group of points where every point may be the landmark with a greater error. To find the most accurate point and identify it as a landmark from the group of points is performed automatically. It is difficult to identify the landmark accurately from the group of points manually. Hence, for increasing accuracy, one point is selected from the group of points by use of the definition of that particular landmark.

In the disclosed embodiments, these drawbacks have been removed and is based on the knowledge derived from the human anatomy. The anatomical definitions are transformed into mathematical entities for the detection of the landmarks which may be different or common for most of the landmarks. The knowledge is derived for each new landmark on the basis of its anatomical structure.

SUMMARY

According to some embodiments, disclosed is a method of automatic landmark detection in three-dimensional data.

According to some embodiments, disclosed is a method of automatic landmark detection in three-dimensional data based on knowledge of human anatomy.

Yet according to some embodiments, disclosed is initialization of the detection of the landmark from a seed point which is a definite point to start search in anatomical geometry.

Still according to some embodiments, disclosed is reduction of search space in every step of the method so that every landmark can be defined in single mathematical entity.

Yet according to some embodiments, disclosed is searching landmark on patient data directly rather than sample image.

Still according to some embodiments, disclosed is providing a more accurate method for automatic cephalometric landmark detection.

Yet according to some embodiments, disclosed is providing a three-dimensional framework for diagnosis and treatment planning of patients.

In an embodiment, a method for detecting a plurality of three-dimensional cephalometric landmarks automatically is disclosed. Said detection is based on Reference Point and two three-dimensional distance vectors calculated from the Reference Point. Selection of corresponding contour and Mathematical Entity are the steps for extracting 3-D coordinate of landmarks.

In another embodiment, a method for automatic detection of plurality of cephalometric anatomical landmarks in volumetric data is disclosed. Said method comprising steps of:
  a. searching a Reference Point;
  b. estimating an Empirical Point;
  c. estimation of VOI (Volume of Interest) based on vector distance from Empirical Point;
  d. detection of structural three-dimensional contours in estimated VOI;
  e. detection of landmark on the detected contour using corresponding mathematical Entity.

In yet another embodiment, said method includes a template comprising hard-tissues and teeth of lower mandible jaw for searching of seed point In still another embodiment, said method includes searching of Reference seed Point in volumetric data.

In yet another embodiment, said method includes the estimation of Empirical Point using vector distance from Reference Point for detection of VOI.

In still another embodiment, said method includes the estimation of VOI using vector distance from Empirical Point.

In yet another embodiment, said method includes the detection of contours by traversing of VOI through Sagittal, Coronal and Axial plane in the direction of X-axis, Y-axis and Z-axis respectively.

In still another embodiment, said method includes the detection of contours by traversing of VOI through the combination of Sagittal, Coronal and Axial plane in the direction of X-axis, Y-axis and Z-axis respectively.

In yet another embodiment, the method of contour identification is prominent point detection on a plane.

In still another embodiment, the method of contour identification is boundary point detection on a plane.

In yet another embodiment, said method includes detection of contour on projected XY-plane, projected YZ-plane and projected XZ-plane of 3-D VOI where coordinate of remaining dimension such as Z, X and Y can be zero respectively.

In still another embodiment, said method includes detection of 3-D landmark comprising of the detection of landmark on plane based on contour followed by detection of corresponding third coordinate.

In yet another embodiment, said method includes contour detection in plurality of VOI.

In still another embodiment, the plurality of three-dimensional points is detected automatically by traversing of volumetric data through Sagittal, Coronal and Axial plane.

In yet another embodiment, the detection of plurality of points by traversing of volumetric data through Sagittal, Coronal and Axial plane is the method of detection of cephalometric anatomical curve.

In still another embodiment, the plurality of three-dimensional points are detected automatically on detected contours of anatomical structure.

In yet another embodiment, the method includes detection of landmarks and reference points by using contour points on the basis of at least one of the following entities:
  a. Searching peak point;
  b. Searching deepest point;
  c. Calculating a mid-point of reference points;
  d. Searching a point of inflection among corresponding contour Points;

e. Determining a point with minimum slope made with a reference point;
f. Determining a point with maximum slope made with a reference point;
g. Determining a centroid of contour;
h. Determining a junction point of plurality of contours;
i. Determining a point among contour points which is nearest to the reference point;
j. Determining a point among contour points which is farthest to the reference point;

In still another embodiment, said method includes dividing the volumetric data in plurality of VOI for searching plurality of landmark.

In yet another embodiment, said method includes dividing the volumetric data in plurality of VOI for searching plurality of contour.

DETAILED DESCRIPTION

Table 1 illustrates required information for searching landmark automatically according to some embodiments.

TABLE 1

| Region No. | Ref. Point | Distance to Empirical Point (mm × mm × mm) | VOI size (mm × mm × mm) | Corresponding Contour(s) | Mathematical Entity | Landmark(s) |
|---|---|---|---|---|---|---|
| Region-1 | Seed Point | 0 × 0 × 0 | 50 × 20 × 42 | Contour made by the initial boundary detection of geometrical structure while traversing XZ-plane sequentially from origin to Y-axis direction | Deepest point in Y-axis direction | B-Point |
| | | | | | Peak point in Y-axis direction after location of the B-point | Pogonion |
| | | | | | Farthest point in negative Z-axis direction | Menton |
| | | | | | Mid-Point of Pogonion and Menton on contour | Gnathion |
| Region-2 | Seed Point | −40 × 30 × 0 | 40 × 65 × 97 | First geometrical contour by traversing XY-plane in Z-axis direction from mid of the VOI | Deepest Point on contour | R3 (Right) |
| | | | | | Peak point in decreasing Y-axis direction | Coronoid (Right) |
| | | | | | Peak point in increasing Y-axis direction | Condylion (Right) |
| | | | | Based on R3 point | Projection point of R3 on geometry in negative Z-axis direction | R4 (Right) |
| | | | | First geometrical contour by traversing XZ-plane in negative Y-axis direction from mid of the VOI | Deepest Point on contour | R1 (Right) |
| | | | | Based on R1 point | Projection point of R1 on geometry in negative Y-axis direction | R2 (Right) |
| | | | | Geometrical contour between R2 and R4 point | A point from group of contour points which has minimum distance on YZ-Plane from nearest vertex of the same plane | Gonion (Right) |
| Region-3 | Seed Point | 40 × 30 × 0 | 40 × 65 × 97 | First geometrical contour by traversing XY-plane in Z-axis direction from mid of the VOI | Deepest Point on contour | R3 (Left) |
| | | | | | Peak point in decreasing Y-axis direction | Coronoid (Left) |
| | | | | | Peak point in | Condylion |

TABLE 1-continued

| Region No. | Ref. Point | Distance to Empirical Point (mm × mm × mm) | VOI size (mm × mm × mm) | Corresponding Contour(s) | Mathematical Entity | Landmark(s) |
|---|---|---|---|---|---|---|
| | | | | | increasing Y-axis direction | (Left) |
| | | | | Based on R3 point | Projection point of R3 on geometry in negative Z-axis direction | R4 (Left) |
| | | | | First geometrical contour by traversing XZ-plane in negative Y-axis direction from mid of the VOI | Deepest Point on contour | R1 (Left) |
| | | | | Based on R1 point | Projection point of R1 on geometry in negative Y-axis direction | R2 (Left) |
| | | | | Geometrical contour between R2 and R4 point | A point from group of contour points which has minimum distance on YZ-Plane from nearest vertex of the same plane | Gonion (Left) |
| Region-4 | Seed Point | 0 × 0 × 50 | 50 × 65 × 40 | Contour made by the initial boundary detection of geometrical structural points while traversing XZ-plane sequentially in Y-axis direction | Sharp peak point on contour in negative Y-axis direction | ANS |
| | | | | | Deepest point on contour after ANS in negative Z-axis direction | A-Point |
| | | | | Contour made by the farthest point in Y-axis while traversing YZ-plane sequentially in X-axis direction | Peak point in Y-axis direction | PNS |
| Region-5 | Seed Point | 0 × 0 × 90 | 50 × 35 × 40 | Contour made by the initial boundary detection of geometrical structural points while traversing XZ-plane sequentially in Y-axis direction | Deepest Point on contour in Y-axis direction | Nasion |
| Region-6 | Nasion | −60 × 0 × −40 | 50 × 25 × 30 | Contour made by the initial boundary detection of geometrical structural points while traversing XY-plane sequentially in Z-axis direction | Deepest Point on contour in negative Z-axis direction | Orbitale (Right) |
| Region-7 | Nasion | 10 × 0 × −40 | 50 × 25 × 30 | Contour made by the initial boundary detection of geometrical structural points while traversing XY-plane sequentially in Z-axis direction | Deepest Point on contour in negative Z-axis direction | Orbitale (Left) |
| Region-8 | Nasion | −20 × 45 × −30 | 40 × 40 × 35 | Contour made by the anatomical | Midpoint of two largest sequential | Sella |

TABLE 1-continued

| Region No. | Ref. Point | Distance to Empirical Point (mm × mm × mm) | VOI size (mm × mm × mm) | Corresponding Contour(s) | Mathematical Entity | Landmark(s) |
|---|---|---|---|---|---|---|
| | | | | boundary in projected YZ-plane (2-D) of VOI | gradients on YZ-plane contour (2-D) for y-and z-axis coordinates; and midsagittal plane is referred for corresponding x-axis coordinate | |
| Region-9 | A-Point | −60 × 10 × −10 | 40 × 25 × 30 | Contour made by the anatomical boundary in projected XZ-plane (2-D) of VOI | A point from group of contour points which has maximum distance on XZ-plane (for x- and z-axis coordinate) from the origin of the VOI and corresponding midpoint of the width of the Jugal process of maxilla is referred for x-axis coordinate | Jugal (right) |
| Region-10 | A-Point | 20 × 10 × −10 | 40 × 25 30 | Contour made by the anatomical boundary in projected XZ-plane (2-D) of VOI | A point from group of contour points which has maximum distance on XZ-plane (for x- and z-axis coordinate) from the origin of the VOI and corresponding midpoint of the width of the Jugal process of maxilla is referred for x-axis coordinate | Jugal (Left) |

Figure 1:
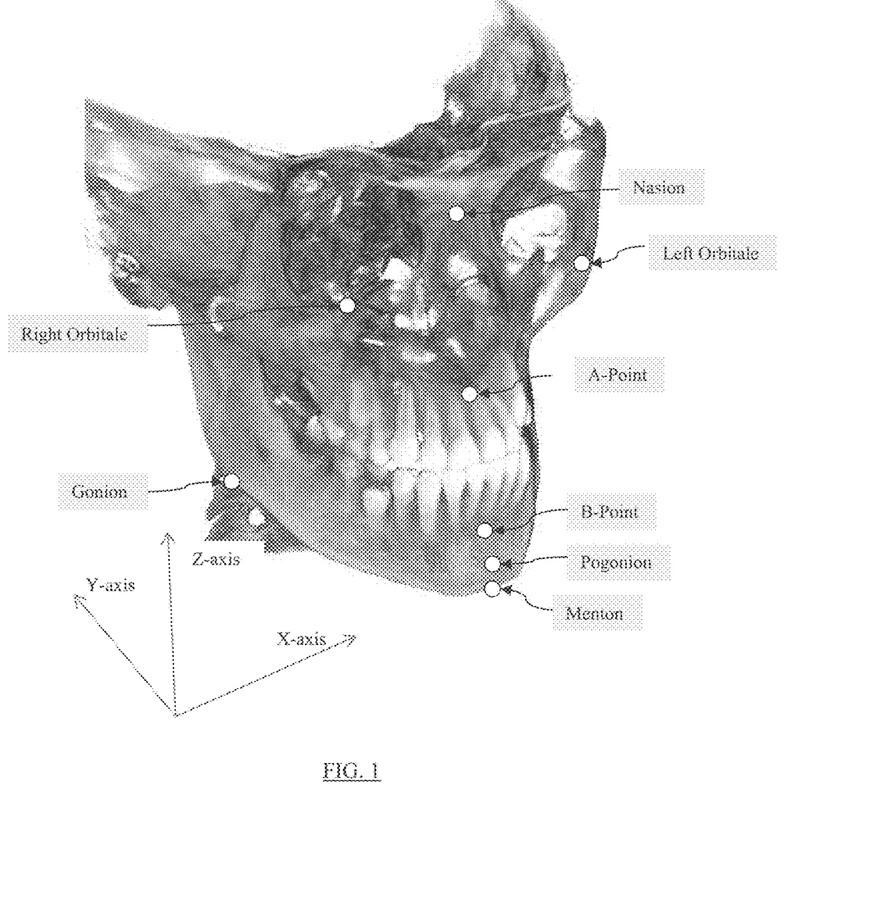
FIG. 1 illustrates a three dimensional model of patient volumetric data with a few manually plotted landmarks according to some embodiments.

A three-dimensional model can be visualized by stacking of two-dimensional slices of volumetric data. The examples of these data are Computed Tomography (CT), Cone Beam CT (CBCT) or Magnetic Resonance Imaging (MRI). These types of data are used in medical diagnosis and treatment planning. Data is uploaded in computer system and a computer program is run over the data and visualizes 2-D slices as well as 3-D anatomy which can be seen in any orientation. In clinical practice, orthodontists used to mark cephalometric landmarks on 3-D volume rendered model and 2-D slices, of volumetric data for cephalometric analysis of the patient. Cephalometric landmarks are the 3-D coordinates of established anatomical location in skull for establishing relationship with standard framework of measurements. Each landmark is plotted manually on either 3-D model or 2-D slices. It takes time and effort to search exact location of landmark. FIG. 1 shows a 3-D skull with few cephalometric landmarks plotted. Some embodiments relate to a method for plotting of landmarks automatically on volumetric data. In one embodiment, the method takes volumetric data as input and exports three dimensional coordinates of automatically detected landmarks.

FIG. 1 shows manual plotting of landmarks on skull according to some embodiments. Few landmarks such as Nasion, Orbitale, A-Point, B-Point, Pogonion, Menton and Gonion have been plotted manually on skull. Some embodiments automatically determine the location of such desired points and export the 3-D coordinates.

Figure 2:
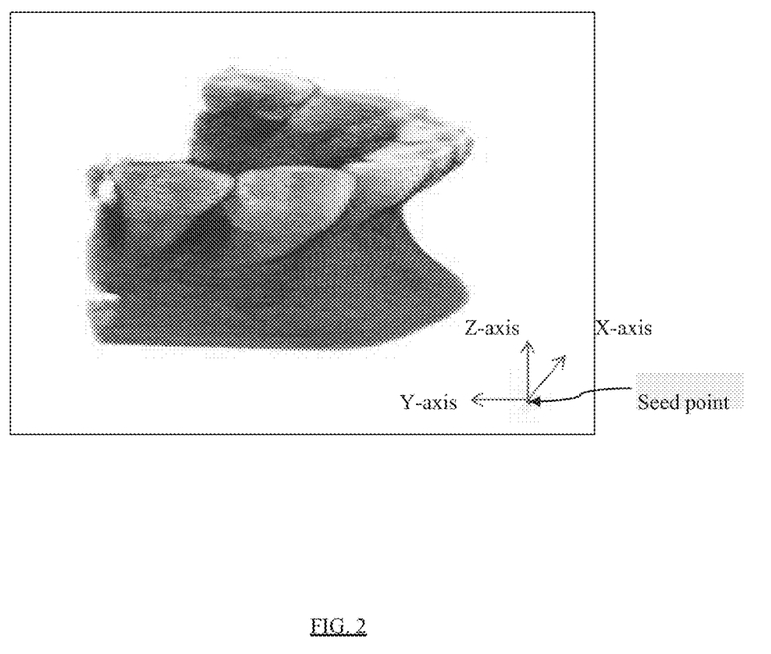
FIG. 2 illustrates a template of lower mandibular region with seed point according to some embodiments.

According to an embodiment, a seed Point is searched in volumetric data. It is an initial Reference point to start searching for landmark detection. Seed point is dependent on distinct geometry in data. Thus, an approach of template matching is adopted for searching a distinguishable region in skull. A template with seed point is developed as shown in FIG. 2 for searching such type of region. Said template comprises hard-tissues and teeth of lower mandible jaw which is most distinguishable in human skull. The template is matched with patient volumetric data to obtain seed point for initialization of landmark searching.

Table 1 shows information for searching of cephalometric landmarks based on a seed Point according to some embodiments. Landmarks are searched in groups and each group is searched in a particular region. First region search is initialized from the seed point, and other regions are searched from either the seed point or the detected landmark. The seed point or detected landmark used for region searching is called as a Reference Point. For a particular region searching, two types of distance vectors are estimated. First distance vector is from Reference Point to Empirical Point, and second distance vector is from Empirical Point for VOI (Volume of Interest) size. Distance vector estimated from Reference Point to Empirical Point makes sure that there is no corresponding landmark belonging to the region existing in between. Distance covered with this vector gives coordinate of Empirical Point, Thus, the geometry between Reference Point and Empirical Point does not have landmark belonging to particular region which has to be found. Then again, distance vector is estimated from the Empirical Point which makes sure that the corresponding group of landmark exists in between. VOI is designed from Empirical Point of the size of estimated distance vector such that anatomical geometry of corresponding landmarks is accommodated, Contours are identified on the detected anatomical geometry of the VOL Corresponding Mathematical Entity is applied to the relevant contour to detect coordinates of landmark as shown in Table 1.

Thus, Table 1 provides VOI, Reference Point, distance vector for Empirical Point estimation, VOI size, corresponding contour and Mathematical Entity for particular landmark search. This information can be used for certain landmark searching. However, the scope of this disclosure is not limited to this information. For example, such type of information can be generated for further landmark detection.

Figure 4:
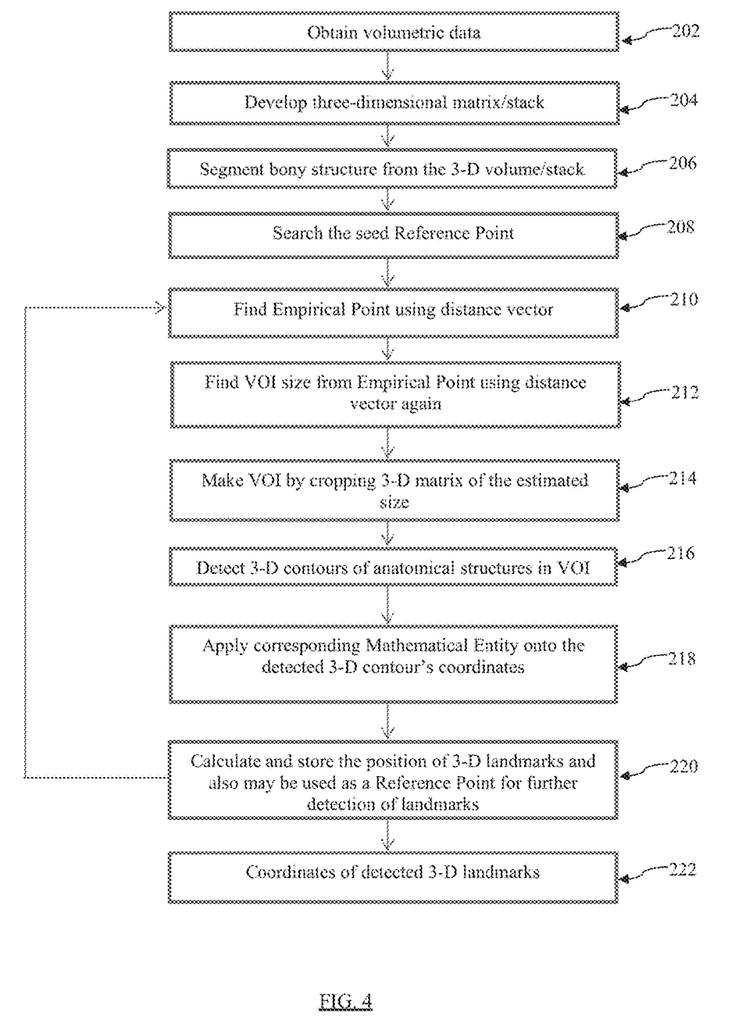
FIG. 4 illustrates a method of three-dimensional automatic landmark detection in volumetric data according to some embodiments.

Present embodiment is composed of certain steps which are performed on patient's volumetric data. FIG. 4 illustrates a method of automatic detection of cephalometric landmarks on volumetric data. At step 202, two-dimensional slices of volumetric data are loaded on computer system's memory, At step 204, all slices are stacked and developed into a three-dimensional matrix. This matrix data is volumetric data of the skull and can be visualized in the form of 3-D model of anatomy. At step 206, bony structure is segmented using Hounsfield Units (HU) threshold value, After segmentation, 3-D matrix contains HU values only for bony structure of given volumetric data.

Three-dimensional matrix is simply thresholded hard-tissue data of skull. It does not have a point of reference for understanding the anatomical geometry. Thus, a template is made for searching a seed point in unknown anatomical geometry for initializing the process of searching. This point is referred to as a seed Point. It may exist anywhere in volumetric data. This is an initializing point of the search process as a Reference Point. At step 208, a seed point is searched in segmented data of stage 206. Seed point is a known anatomical geometrical point from where Empirical Point is estimated. Some embodiments use template matching method for searching of seed point. A template comprising lower mandible region is used for searching a seed point in volumetric data as shown in FIG. 2. This shows only an example of template matching for determining Reference seed Point. However, the process of determining Reference seed Point can also be performed by other methods of image processing and pattern matching. To search a seed point for finding Empirical Point comes under the step 208.

At step 210, Empirical Point is found using distance vector from the reference of seed point. This is the maximum distance from Reference Point which does not contain belonging landmark of the particular region. At step 212, again a distance vector is estimated from the empirical point for accommodating a desired group of landmarks. This distance vector develops a Volume of Interest (VOI), VOI is sufficient in size that corresponding group of landmarks exists in it.

At step 214, vector distance is cropped and obtains a volume of interest (VOI). At step 216, three-dimensional contours are detected by tracing anatomical structure of VOI. Contours are detected by traversing of VOI either one or in combination of Sagittal, Coronal and Axial plane in the direction of X-axis, Y-axis and Z-axis respectively. Prominent point detection on a plane and boundary point detection on a plane are other methods for detecting contours in VOI. It is not necessary to trace all contours of the VOL For reducing complexity of the method, only required contours can be traced where desired landmark resides.

Figure 3:
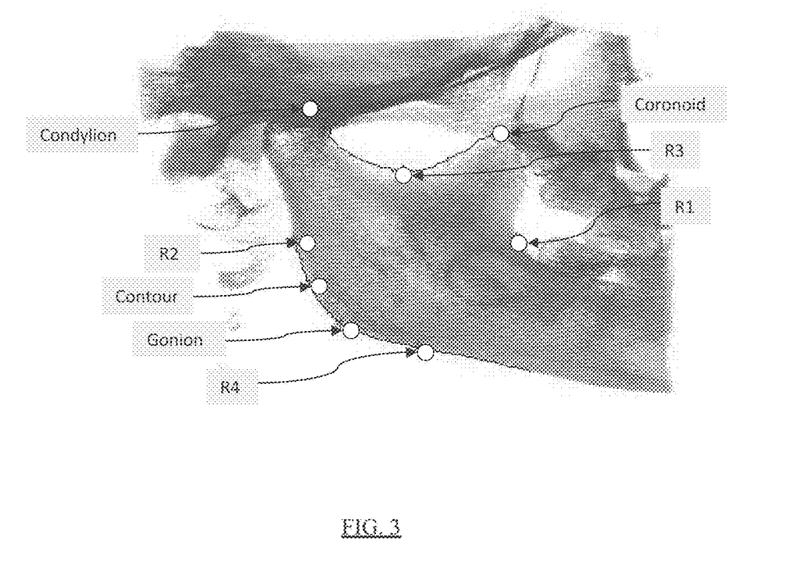
FIG. 3 illustrates volume of interest (VOI) with few detected contours for landmark detection in mandibular region according to some embodiments.

FIG. 3 shows an example of VOL This VOI is developed for detecting cephalometric landmarks on right ramus of mandible region. Few contours are shown on structural boundaries of VOL Corresponding Mathematical Entity is applied on three-dimensional coordinates of contours. Using Mathematical Entities, few exemplary landmarks are detected as shown in FIG. 3. These landmarks are known as R1, R2, R3, R4, Coronoid, Condylion and Gonion.

Returning to FIG. 4, at step 218, corresponding Mathematical Entity is identified as shown in table 1, for each desired cephalometric landmark using the detected contours in VOL Said Mathematical Entity is the way to distinguish a point from its group of contour points. Some Mathematical Entities are given below which are used to identify a landmark correspondingly from the contour points.

a) Searching peak point; b) Searching deepest point; c) Calculating a mid-point of reference points; d), Searching a point of inflection among corresponding contour Points; e) Determining a point with minimum slope made with a reference point; f) Determining a point with maximum slope made with a reference point; g) Determining a centroid of contour; h) Determining a junction point of plurality of contours; i) Determining a point among contour points which is nearest to the reference point; j) Determining a point among contour points which is farthest to the reference point.

At step 220, coordinates of the desired cephalometric landmarks are obtained using the Mathematical Entity in stage 218, Obtained landmarks are stored in program variable and can be used as a reference point for further detection of landmarks. Detected landmarks can be used as a Reference Point for input of stage 210 for further detection of landmarks in next iteration. Similarly, the same process as described earlier is processed for further detection of remaining landmarks. This process is in a loop till all the desired landmarks are detected. A Reference Point can also be used to make plurality of VOIs at different times. Additionally plurality of Reference Points can be used to define one VOI.

The above described method is run with the computer program. Patient data is stored in computer memory or external memory attached to the computer system. At stage 222, coordinates for all desired detected landmarks are obtained through the computer program. These coordinates of landmarks can be input into any other software or computer program, and visualized the landmark on patient's data. This process can be helpful for assisting orthodontist for cephalometric analysis. Time for landmark plotting and corresponding efforts can be reduced for the same.

Some embodiments relate to the process of landmark detection for cephalometric analysis. While these and other embodiments have been described, these embodiments have been presented by way of example only, and are not intended to limit the scope of the protection. Indeed, the novel methods and systems described herein may be embodied in a variety of other forms. Furthermore, various omissions, substitutions and changes in the form of the methods and systems described herein may be made without departing from the spirit of the protection. The accompanying claims and their equivalents are intended to cover such forms or modifications as would fall within the scope and spirit of the protection. For example, embodiments of the automatic landmark detection method can be used in other volumetric data also for detecting landmarks. Various processes and/or components illustrated in the figures may be implemented as software and/or firmware on a processor, ASIC/FPGA, or dedicated hardware, which can include logic circuitry. The software and/or firmware can be stored on a non-transitory computer readable storage, such as for example in internal or external memory. Additional system components can be utilized, and disclosed system components can be combined or omitted. The actual steps taken in the disclosed processes, such as the process illustrated in FIG. 4, may differ from those shown in the figures. Depending on the embodiment, certain of the steps described above may be removed, others may be added. Also, the features and attributes of the specific embodiments disclosed above may be combined in different ways to form additional embodiments, all of which fall within the scope of the present disclosure. Although the present disclosure provides certain preferred embodiments and applications, other embodiments that are apparent to those of ordinary skill in the art, including embodiments which do not provide all of the features and advantages set forth herein, are also within the scope of this disclosure. Accordingly, the scope of the present disclosure is intended to be defined only by reference to the appended claims.

EXAMPLES

The following examples are for illustration purposes only and do not cover or reflect the full scope of present disclosure, which is defined by the claims.

Example 1

A three-dimensional matrix is developed with sectional slices of CBCT data. This matrix contains HU values of geometrical anatomy of skull. Bony structure of the skull is segmented using thresholding HU value as 226. A seed point is searched using template searching method with correlation measurement. It is identified towards origin of the best searched region and anatomically available below chin. This seed point is considered as reference point for initializing the searching of landmarks. Empirical point is found at 0×0×0 distance from the reference point. A volume of interest (VOI) of size 50 mm×20 mm×42 mm is picked out from empirical point. This is the first region for detection of B-Point, Menton, Pogonion, Gnathion landmarks. A contour is made in VOI by the detection of initial boundary of geometrical structure while traversing XZ-plane sequentially from origin in Y-axis direction. Corresponding mathematical entity is selected for obtaining the coordinates of particular landmark. Deepest point in the Y-axis direction is identified as B-point. Peak point in Y-axis direction after location of the B-point is identified as Pogonion point. Farthest point in negative Z-axis direction is identified as the Menton point, Mid-point of Pogonion and Menton on contour is identified as Gnathion.

Example 2

Empirical point is identified at −40 mm×30 mm×0 distance vector from the seed reference point and VOI is designed a size of 40 mm×65 mm×97 mm. First geometrical contour is selected by traversing XY-plane in Z-axis direction from mid of the VOI. The deepest point on the contour is identified as right R3 point, peak point in decreasing Y-axis direction is identified as right Coronoid point and peak point in increasing Y-axis direction is identified as right Condylion point. Projection point of R3 on geometry in negative Z-axis direction is identified as right R4 point. First geometrical contour is selected by traversing XZ-plane in the negative Y-axis direction from mid of the VOI. The deepest point on contour is identified as right R1 point and projection point of R1 on geometry in negative Y-direction is identified as right R2 point. Geometrical contour between R2 and R4 point is selected and a point is detected from group of contour points which has minimum distance on YZ-Plane from nearest vertex of the same plane is known as right Gonion point.

Example 3

Empirical point is identified at 0×0×50 mm from the seed point and VOI is designed of size 50 mm×65 mm×40 mm. First contour is made by the initial boundary detection of geometrical structural points while traversing XZ-plane sequentially in Y-axis direction. A sharp peak point on contour in negative Y-axis direction is identified as ANS point and deepest point on contour after ANS in negative Z-direction is identified as A-point. A contour is made by selecting the farthest point in Y-axis while traversing YZ-plane sequentially in X-axis direction. PNS point is identified as a peak point in Y-axis direction on this contour.

Example 4

Empirical point is identified at 0×0×90 mm vector distance from the seed point and designed a VOI of size 50 mm×35 mm×40 mm. A contour is made by the initial boundary detection of geometrical structural points while traversing XZ-plane sequentially in Y-axis direction. The deepest point on the contour in Y-axis direction is identified as Nasion point.

One advantage is that it uses a seed point to initialize the search process which is a definite and unique point for identification of anatomical geometry.

Another advantage is that it proposes the hierarchical search method which reduces the search space in each stage.

Another advantage is that it is based on the knowledge generated from human anatomy.

Another advantage is that it searches the landmark by traversing each slice which is the smallest transaction unit.

Another advantage is that it provides assistance for 3-D cephalometric analysis for orthodontists.

Another advantage is that it saves time for 3-D cephalometric analysis.

What is claimed is:

1. A computer-implemented method for fully automatic detection of a plurality of 3D cephalometric landmarks on anatomical structures in volumetric data comprising of prior knowledge derived from mathematical entities and steps, wherein the method comprises:

receiving three dimensional model data, wherein the three dimensional model data includes one or more of: computed tomography data (CT) produced by a CT scanner, cone beam computed tomography (CBCT) data produced by a CBCT scanner, or magnetic resonance imaging (MRI) data produced by an MRI scanner generating scan volumetric data of the skull of a patient;

detecting a Reference Point in a given volume in the three dimensional model data;

estimating an Empirical Point in the given volume based on a first vector distance from the Reference Point, wherein the Empirical Point comprises a point of maximum distance from the reference point;

estimating a VOI (Volume of Interest) in the given volume based on a second vector distance from the Empirical Point, wherein the VOI comprises a subset of the given volume;

cropping the three dimensional model data for the VOI;

detecting structural three-dimensional contours in the cropped VOI using the mathematical entities applied individually on each 2D slice stacked as three dimensional model data;

detecting a landmark on one of the detected structural three-dimensional contours by performing a hierarchical search of a plurality of mathematical entities that includes:

identifying a first point based on a first mathematical entity from the Reference Point, wherein the identifying includes identifying a point on the one of the detected structural three-dimensional contours from the Reference Point in Y-axis direction as the first point;

identifying a second point based on a second mathematical entity from the first point, wherein the identifying includes identifying a point on the one of the detected structural three-dimensional contours from the first point in the Z-axis direction as the second point; and identifying the landmark based on a third mathematical entity from the second point, wherein the identifying includes identifying a mid-point between the second point and a third point as the landmark; and transmitting the landmark to a display for displaying the first point, the second point, and the detected landmark on the three dimensional model data to a user in order to facilitate 3-D cephalometric analysis of the anatomical structure, wherein the display is configured to display a plurality of two-dimensional slices of volumetric data stacked into a three-dimensional model and further display the first point, the second point, and the landmark within the three-dimensional model.

2. The method of claim 1, further comprising providing a volumetric template for detecting the first reference point called seed point which includes hard-tissues and teeth of lower mandible jaw and matching the template with the VOI to identify the seed point uniquely in a patient's three dimensional model data.

3. The method of claim 1, further comprising automatic detection of the Reference Point in three dimensional volumetric data.

4. The method of claim 1, further comprising estimating the Empirical Point using the first vector distance from the Reference Point for detection of the VOI.

5. The method of claim 1, further comprising estimating the VOI using the second vector distance from the Empirical Point.

6. The method of claim 1, further comprising detecting contours by traversing of the VOI through Sagittal, Coronal and Axial plane in the direction of X-axis, Y-axis and Z-axis respectively.

7. The method of claim 1, further comprising detecting contours by traversing of the VOI through the combination of Sagittal, Coronal and Axial plane in the direction of X-axis, Y-axis and Z-axis respectively.

8. The method of claim 1, wherein the detecting of the 3D contours uses locus of prominent points on stacked planes.

9. The method of claim 1, wherein the detecting of the 3D contours uses boundary point detection on each stacked plane of the VOI.

10. The method of claim 1, further comprising detecting contours on a projected XY-plane, a projected YZ-plane and a projected XZ-plane of the VOI where coordinates of a remaining dimension such as Z, X and Y can be zero respectively.

11. The method of claim 1, further comprising detecting a landmark which includes detecting the landmark on plane based on the contours followed by detection of corresponding third coordinate.

12. The method of claim 1, wherein detecting the structural three-dimensional contours comprises automatically detecting of a plurality of three-dimensional points by traversing of volumetric data through Sagittal, Coronal and Axial plane.

13. The method of claim 12, wherein detecting the structural three-dimensional contours further comprises detecting of a plurality of three-dimensional points by traversing of volumetric data through Sagittal, Coronal and Axial plane to detect a cephalometric anatomical curve.

14. The method of claim 1, further comprising automatically detecting of a plurality of three-dimensional points on the detected contours of an anatomical structure.

15. The method of claim 1, wherein each of the first, second, and third mathematical entities comprise at least one of:

detection of a peak point among a group of contour points;

detection of a deepest point among the group of contour points;

computing a mid-point of already detected two reference points;

detecting a point of inflection among corresponding contour Points;

determining a point among the group of contour points with a minimum slope made with a reference point;

determining a point among the group of contour points with a maximum slope made with a reference point;

determining a centroid of a contour from the group of contour points;

determining a junction point of a plurality of contours;

determining a point among contour points which is nearest to the reference point; or determining a point among contour points which is farthest to the reference point.

16. The method of claim 1, wherein detecting the landmark comprises dividing a volumetric data in the VOI to generate a subset of the volumetric data.

17. The method of claim 1, detecting the structural three-dimensional contours comprises dividing a volumetric data in the VOI to generate a subset of the volumetric data.

18. The method of claim 1, wherein the Empirical Point comprises a point of maximum distance from the reference point not including the landmark of the given volume.

19. The method of claim 1, wherein the method is performed without using a training set.

* * * * *